United States Patent [19]
Miller

[11] Patent Number: 6,146,591
[45] Date of Patent: Nov. 14, 2000

[54] BIOCHEMICAL DETECTION SYSTEM FOR RAPID DETERMINATION OF THE PRESENCE OF TOXINS, BACTERIA, AND OTHER SUBSTANCES

[76] Inventor: C David Miller, 44 Lakeside Dr., Greenbelt, Md. 20770

[21] Appl. No.: 09/070,737

[22] Filed: May 1, 1998

[51] Int. Cl.[7] .......................... G01N 21/00; G01N 35/02
[52] U.S. Cl. ................................. 422/65; 422/58; 422/56; 422/57; 422/63; 422/100; 422/101; 436/44; 436/46; 436/47; 436/49; 436/165; 436/169; 436/177; 436/178; 436/180
[58] Field of Search ..................... 422/919, 920, 422/921, 922, 923, 925, 926, 58, 56, 57, 63, 65, 82.05, 100, 104, 102, 101; 436/44, 47, 49, 165, 169, 177, 178, 180

[56] References Cited

U.S. PATENT DOCUMENTS

| | | | |
|---|---|---|---|
| 4,106,911 | 8/1978 | Marcelli | 23/259 |
| 4,158,035 | 6/1979 | Haase et al. | . |
| 4,215,092 | 7/1980 | Suovaniemi et al. | . |
| 4,569,235 | 2/1986 | Conkle et al. | . |
| 4,576,054 | 3/1986 | Lalin | . |
| 4,589,292 | 5/1986 | Delhaye et al. | . |
| 4,827,780 | 5/1989 | Sarrine et al. | 73/864.21 |
| 5,053,197 | 10/1991 | Bowen | 422/58 |
| 5,101,670 | 4/1992 | Steger et al. | . |
| 5,158,895 | 10/1992 | Ashihara et al. | 436/526 |
| 5,607,861 | 3/1997 | Komatsu et al. | 436/50 |
| 5,650,122 | 7/1997 | Harris et al. | 422/81 |
| 5,891,396 | 4/1999 | Karl et al. | 422/65 |
| 5,897,837 | 4/1999 | Mizuno | 422/100 |

*Primary Examiner*—Jill Warden
*Assistant Examiner*—Patricia Kathryn Bex
*Attorney, Agent, or Firm*—Jonathan E. Grant; Grant Patent Services

[57] ABSTRACT

This device discloses a portable sequential contaminant detection system which can test samples for contaminants at predetermined timed intervals. The detection system has a motor to advance a matrix, a motor to raise and lower syringes holding liquefied samples of air to be tested, and a motor to raise and lower plungers within the syringes to draw up fluids or expel fluids into reservoir wells of the matrix to test air or other samples for contaminants. The system relies upon a "matrix" which will hold reagents with which the air samples will be mixed. The matrix is stepped to move into precise registration with the "read" module where the relative reflectance of each capture membrane reads statically by a fixed LED, silicon photodiode and amplifier associated with each channel.

13 Claims, 7 Drawing Sheets

BIOCHEMICAL DETECTION SYSTEM FOR RAPID DETERMINATION OF THE PRESENCE OF TOXINS, BACTERIA, AND OTHER SUBSTANCES

The government has rights in this invention pursuant to contract DAAA15-91-C-0073, awarded by the U.S. Army Chemical Biological Defense Command.

BACKGROUND OF THE INVENTION

1. Field of the Invention

This device discloses a portable sequential contaminant detection system which can test samples for contaminants at predetermined timed intervals.

2. Background of the Invention

Over the years, there have been a number of different sampler devices created to improve the ease and accuracy of testing for air-borne contaminants.

U.S. Pat. No. 4,569,235 (Conkle et al.) discloses a portable sequential air sampler having an easily transportable housing containing therein a plurality of interrelated components which allow the air sampler to operate by either a battery or line power. The components include a vacuum pump and rotary valve which are capable of sequentially drawing air through the sampling media. The flow rate control system is operably connected to the vacuum pump in order to maintain the substantially constant flow rate through the sampling media. The air sampler can vary initiation of the sampling operation from 1–999 minutes while varying the sequence of sampling from 1–99 minutes. while maintaining substantially constant air flow through the air sampling procedure.

U.S. Pat. No. 4,576,054 (Lalin) discloses a dual mode gas sampler and pneumatic flow control system. The device has a manually adjustable flow restricting orifice, a two position mode select valve, a flow controller, and a vacuum pump for drawing gas from the atmosphere through a load representing either a single test article with flow being held constant or multiple test articles with pressure head constant.

U.S. Pat. No. 4,589,292 (Delhaye et al.) discloses a process for sampling ambient air at a work place. The process comprises continually withdrawing by means of a pump, a sample of ambient air in the proximity of the respiratory tract of an individual worker filtering the aspirated air for subsequent analysis of filtered-out particles, picking-up the cardiac rhythm of the individual and controlling the flow air of the pump by a signal modulated by the cardiac rhythm of the individual. The apparatus for carrying out this process comprises a sampling tube, a motor driven pump for drawing a sample of ambient air in through the sampling tube, a filter associated with the sampling tube for filtering the air sample, a photo electric device for picking up the cardiac rhythm of the individual and a control circuit for controlling the flow-rate of the pump by a signal modulated by the cardiac rhythm of the individual.

U.S. Pat. No. 5,101,670 (Steger et al.) discloses an automated sampling system for proportional sampling of a fluid stream. The system includes at least one syringe type sampler container having an inlet and outlet at one end and a piston therein displaceable to fill and discharge the container, means for connecting the inlet of the sample container to the fluid stream, for withdrawing samples to the container, flow sensor means positionable in the fluid stream for continuously measuring the flow rate of the fluid stream and providing a continuous first control signal varying in accordance with the measured flow rate, a piston drive means for withdrawing the syringe piston at a rate in accordance with the first control signal, and limited means for stopping the withdrawing displacement of the piston at a predetermined end point in its axial movement.

U.S. Pat. No. 4,158,035 (Haase et al.) discloses a multiple sample micropipette. The device comprises a housing, a plurality of tubes mounted on the housing, each of the tubes having a passage extending therethrough, flexible impervious membrane means extending across the passages to divide each of the passages into a first passage section and a second passage section, an incompressible flowable material. A mechanism is provided for moving the flowable material to deflect the membrane in opposite directions whereby liquid can be drawn into and expelled from the tubes.

U.S. Pat. No. 4,215,092 (Suovaniemi et al.) discloses a multichannel pipette disclosed having an improved arrangement of replaceable tip containers in which the individual tip containers are connected together by flexible connecting members which are deformable to permit connection of the tip containers to differing configuration of tip cones.

SUMMARY OF THE INVENTION

It is an object of the invention to provide a system for determining the presence and concentration of specific contaminants in a 1 to 2 minute time period in fluid concentrates from an associated sampling device capable of impacting large volumes into small volumes of liquids.

It is another object of the invention to provide a detection system capable of assaying the air/liquid concentrates without requiring external fluids or reagent solutions.

It is another object of the invention to concentrate the contaminants of the sample in a small volume of liquid without the need for external fluids or reagents.

To meet these objectives, the present invention discloses a biochemical detection system having a motor to advance a matrix, a motor to raise and lower syringes holding liquid concentrates to be tested, and a motor to raise and lower plungers within the syringes to draw up fluids or expel fluids into reservoir wells of the matrix to test samples for contaminants. The system will rely upon a "matrix" which will hold reagents with which the samples will be mixed. The matrix will be stepped to move into precise registration with the "read" module where the relative reflectance of each capture membrane will be read statically by a fixed LED, silicon photodiode and amplifier associated with each channel.

The device will be fixed to determine presence and concentration levels of at least four (4) analytes at slightly less than two minute intervals. The unit will be operable from a 24 V DC source or less with continuous power consumption of 5 watts (or less) and will be designed to absolute minimum size and weight constraints.

DETAILED DESCRIPTION OF THE INVENTION

Referring to FIGS. 1–10, the biochemical detection system 1 for the rapid determination of the presence of toxins, bacteria, and other substances principally consists of two main sections. The mechanical drive unit 2 gathers, dispenses, and reads the sample concentrate and the matrix 5 serves as the receptacle for the concentrates which are mixed with reagents and processed.

The drive unit 2 is relatively compact. The drive unit 2 is approximately 6" to 10" long and about 4" to about 8" wide. The device is mounted to a baseplate 3 with the mechanical drive assemblies. The unit 2 is about 6" to 8" high, and weighs from about 4 pounds to 10 pounds. The unit can be operated from a power source consisting of a single 9 volt battery 4 since maximum power consumption during any portion of the cycle, except for the five second read operation, was less than five watts.

Figure 10:
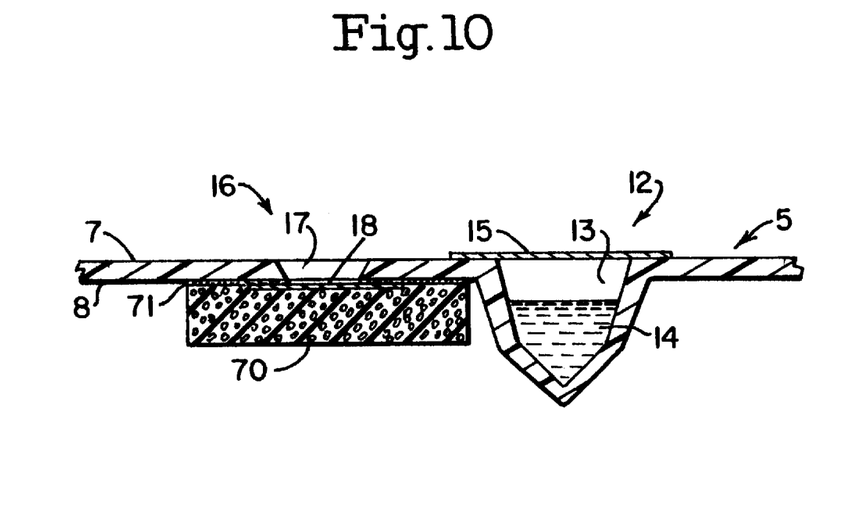
FIG. 10 is an enlarged schematic view of the side view of the matrix.

The matrix 5 comprising a plurality of wells, is a relatively flat rectangularly shaped tray 6 having a top section 7, a bottom section 8, and sides 9. The top section 7 has a first row 10 forming a single trough type reservoir well 11, and a second row 12 having a plurality of individual wells 13. The top section 7 may have sprockets 60 to assist in the advancement of the matrix 5. Each of the individual wells 13 of the second row 12 contains a lyophilized reaction mixture 14 in the second row 12. The wells 13 containing the lyophilized reaction mixture 14 are covered by a secured frangible covering 15, such as a foil, which protects the lyophilized reaction mixture 14 from contamination before use. The third row 16 contains capture membrane wells 17. The capture membrane wells 17 contains a flow through membrane 18 having an absorbent pad 70 which is adhered to the bottom 8 of the matrix 5 by an adhesive layer 71 which captures and traps unreacted conjugate in the membrane. Analyte-conjugate complex remains on the surface of the membrane. In another embodiment of the invention, the membrane may be coated with an antibody or an antigen so that a sandwich assay results. In an alternative embodiment of the invention, the membrane may be coated with an antibody or antigen coated latex, also resulting in a sandwich assay.

In another embodiment of the invention, The membrane may also cause a trapping of the antigen-antibody labeled complex by size or by weight.

The drive unit 2 comprises a plurality of syringes 21 containing plungers 23. The drive unit is also comprised of three motors. One "matrix" motor 19 forwardly advances the matrix 5 by means of a friction drive wheel 43. A second "syringe" motor 20 raises and lowers syringes 21 which are used to collect and expel samples and reagents. A third "plunger" motor 22 raises and lowers the plungers 23 within the syringes 21 to draw in or expel reagents and samples. The preferred syringes were of the plastic 1 cc tuberculin type with barrels and plungers cut to appropriate lengths. These were fitted with ⅝" Luer-hub needles 53 and the entire assembly became very easy to replace, if necessary.

The plurality of syringes 21 are positioned on a support stand 24 having a support bar 25 connected to the plurality of syringes 21. The support bar 25 in turn is raised or lowered by a cam connected to the syringe drive motor 20, such that the syringes 25 may be raised or lowered by the actions of the syringe motor.

Similarly, raising or lowering of the syringe plungers 23 may also be performed by means of a motor driven cam, which raises and lowers a support bar 44 connected to the plungers.

The drive motors selected for the three translational operations were Canon variable speed gear motors providing selectable speeds of 4 rpm to 84 rpm over an input voltage range of 1.5 vdc to 12 vdc. As an alternative to the gear motors, stepper motors could be used.

Figure 9:
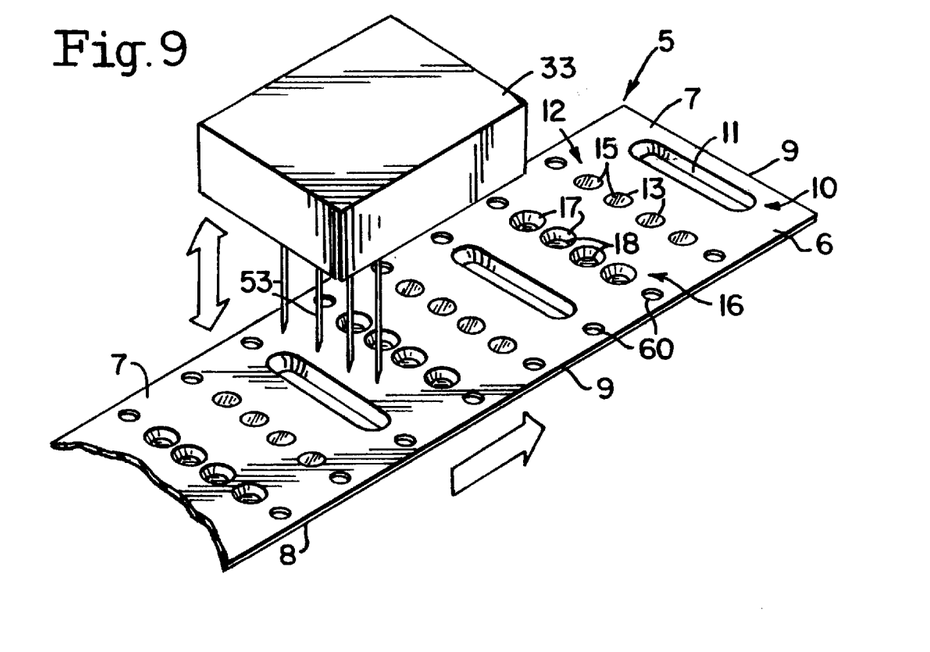
FIG. 9 is an angular, schematic view of the read module.

A reflectanc-base detection unit 32 projects light onto the third row 17, whereupon the reflected light is read by a channel reflectance read head 33. The light wavelength can be changed by replacing the detector unit.

Alternative means may be used to read and detect positive test results. Similarly, other means may be used to raise and lower the plungers and syringes.

The plurality of the support bar 25, support stand 24, syringe motor 20, plunger motor 22, matrix motor 19, and matrix 5, all reside on top of a platform 26, which is secured to the top part of the mechanical drive unit 2. The platform 26 is preferably an aluminum base, having a slot 34 ½"×4"× 7". The front 27 of the mechanical drive unit 2 contains the control panel 28 and operating lights 29. The control panel 28 contains a power switch 35, a cycle-initiate switch 36, a secondary switch 37 to provide the option of single-cycle-and-halt operation or continuous operation, a matrix advance switch 38, a read operation LED 39, four discrete LED's 40 indicative of any reflectance reading lower than the preset threshold value of each channel, indicating a positive response and an associated sonalert device 41 with an on/off switch 42.

Inside of the control unit 2 in the control unit box 30 is the operating system 31 of the entire detection system 1.

Figure 8:
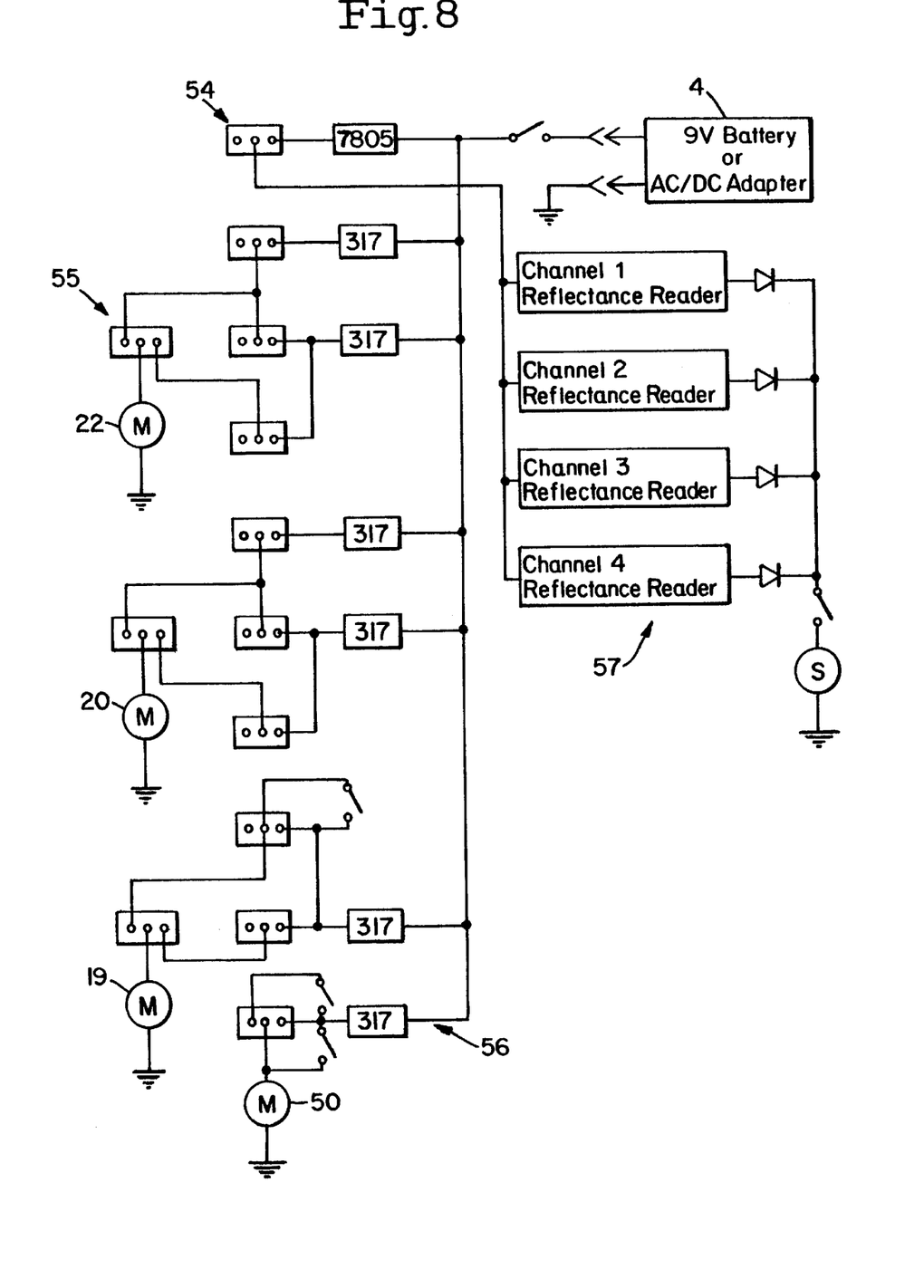
FIG. 8 is a schematic illustration of the general circuit layout for the motion sequence and read head activation.

Because of the advantages of extremely low system power consumption, low current/high torque DC gear motors are chosen to implement all motion sequences thus obviating the problems associated with conventional higher current/lower torque stepper motors. One motor, fitted with a frictional drive wheel 43, was employed for lateral translation of the matrix 5. Second and third motors fitted with cams and followers were utilized to raise and lower spring-loaded blocks which served as drivers for the syringes and plungers. A fourth motor 50 is coupled to an additional geared speed reduction mechanism 51, and, in turn, to a drum programmer 52 which effected all timing and sequencing operations. The drum is constructed from a 1⅛ D×1⅝ L aluminum cylinder drilled and tapped in 240 positions for appropriate insertion of activating pins 58. Twenty three pins 58 were required for controlling all mechanical functions and, in addition to insuring high reliability performance, the system allowed complete or partial reprogramming in less than three minutes. As shown in FIG. 8, ten micro switches 54, each associated with a specific mechanical or switching operation and each activated by corresponding pins on the rotating drum, are used to supply power to distribution points at appropriate time intervals. Single pole, double throw switches 55 are used in conjunction with detented cams to provide separate speed controls for "up" and "down" motions of syringes and plungers.

The drum programmer was chosen for implementation of the timing and sequencing operations because of its reliability, low cost, and ease of programming. It would be obvious, however, to one skilled in the art, that many other means, such as a micro controller, could be utilized to perform these functions.

Figure 7:
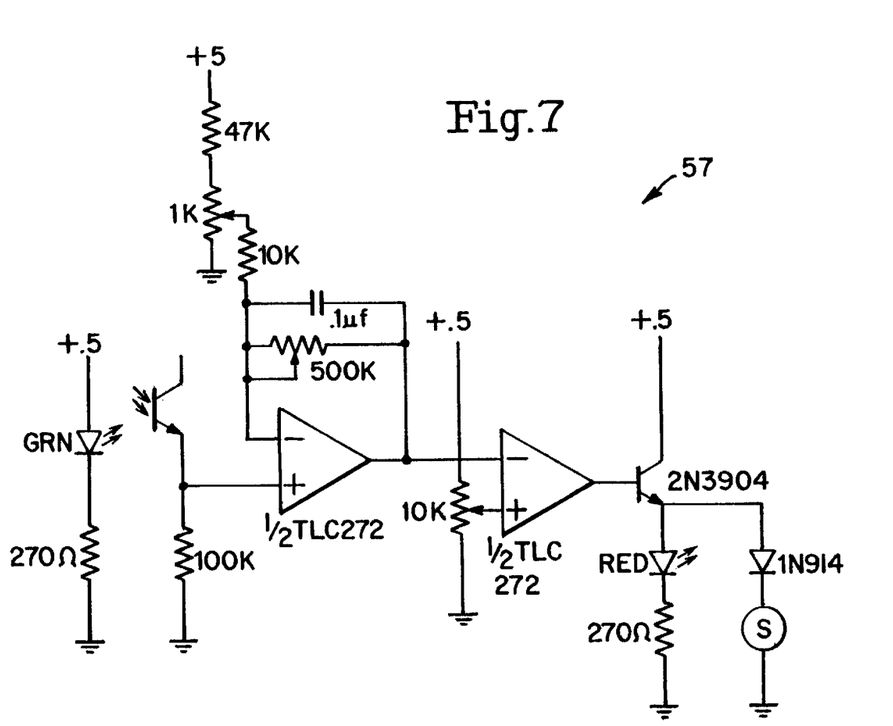
FIG. 7 is a schematic illustration of the reflective reader head circuit.

The electronics consisted of six individually settable voltage regulators 56, four of which are adjusted to provide and maintain appropriate cam follower speeds for the "up" motion and the "down" motion of the syringe drive and plunger drive mechanisms. The fifth regulator is used to set the motor drive speed for advancement of the matrix, and the sixth is used to adjust the drug programmer speed to exactly one revolution per two minutes (the cycle time required for completion of each series of assays). A fixed 5V regulator provides power to each channel of the four position reflectance reader 57 and to the associated indicator LED and sonalert circuitry. Each channel of the reflectance reader consists of a high intensity green LED with a maximum emission wavelength at 563 nm (the region of maximum absorbance for colloidal gold) and a fixed gain phototransistor. The output signal from the phototransistor was fed into a non-inverting amplifier with adjustable gain and background suppression. The amplified signal was fed into a comparator circuit with an adjustable threshold (predetermined for each analyte) and the output in response to a positive (low reflectance) signal turned on a transistor to power the sonalert 41 and the channel-identifying LED 40.

Virtually any sampler capable of impacting or concentrating large volumes of sample into relatively small volumes of fluid may be utilized with the Biochemical Detection System. The instrument applies, at the appropriate time, a voltage signal to an associated solenoid valve or fluid metering device which in turn delivers approximately 400 µl of sample to a reservoir well in the matrix exactly once every two minutes in preparation for the initiation of a new analysis cycle.

The sequence of steps in the operation of the device consists of the timer opening the solenoid valve to deliver air sampler fluid to a matrix reservoir. A pulse is initiated to drive the syringes into the down position into the reservoir well. A second pulse raises the syringe plunger. A following pulse raises the entire syringe.

From there, a pulse advances the matrix one step (or row), and a pulse is provided to lower the syringes, piercing the seals covering the reagent wells. Another pulse lowers the syringe plungers, thereby reconstituting the lyophilized reagents and initiating the reaction. After a pre-set reaction period, a pulse is provided to raise the syringe plungers, and a following pulse is provided to raise the syringes.

Following this step, a pulse advances the matrix one step, and another pulse lowers the syringe plungers. A final pulse advances the matrix one step. A timer initiates the "read" process, during which the samples are read, and the cycle is restarted.

Figure 1:
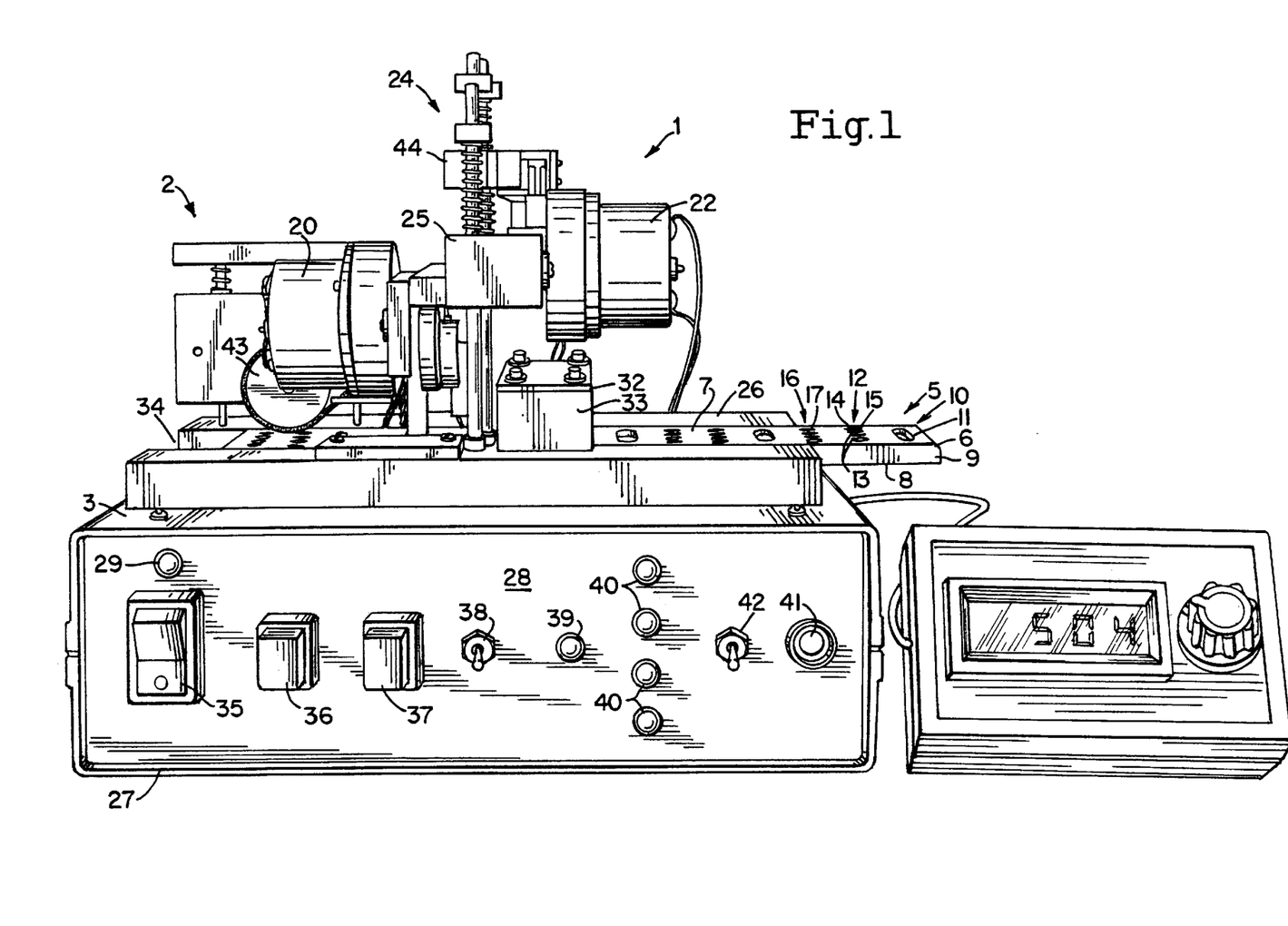
FIG. 1 is a longitudinal view of the invention.
Figure 2:
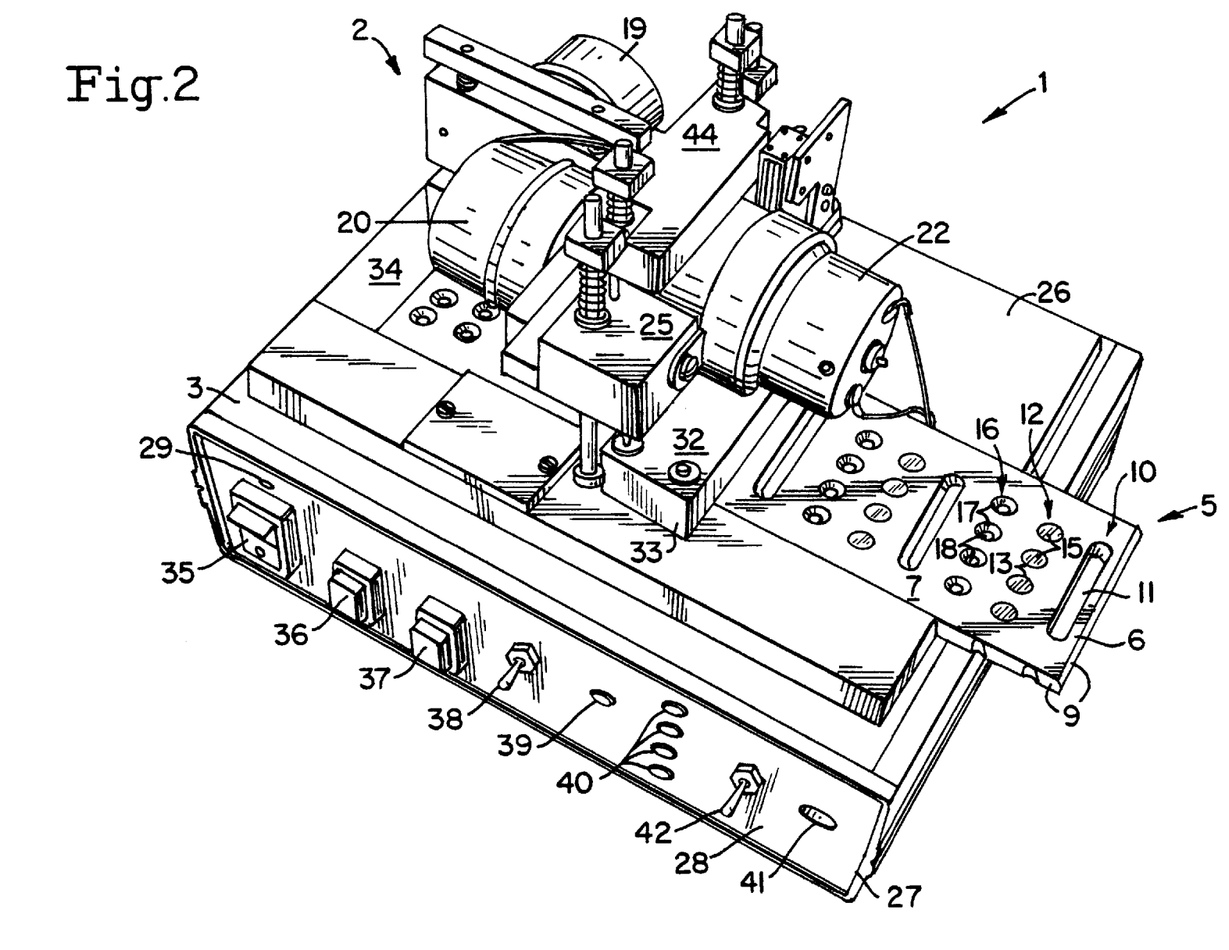
FIG. 2 is an angular overhead view of the invention.
Figure 3:
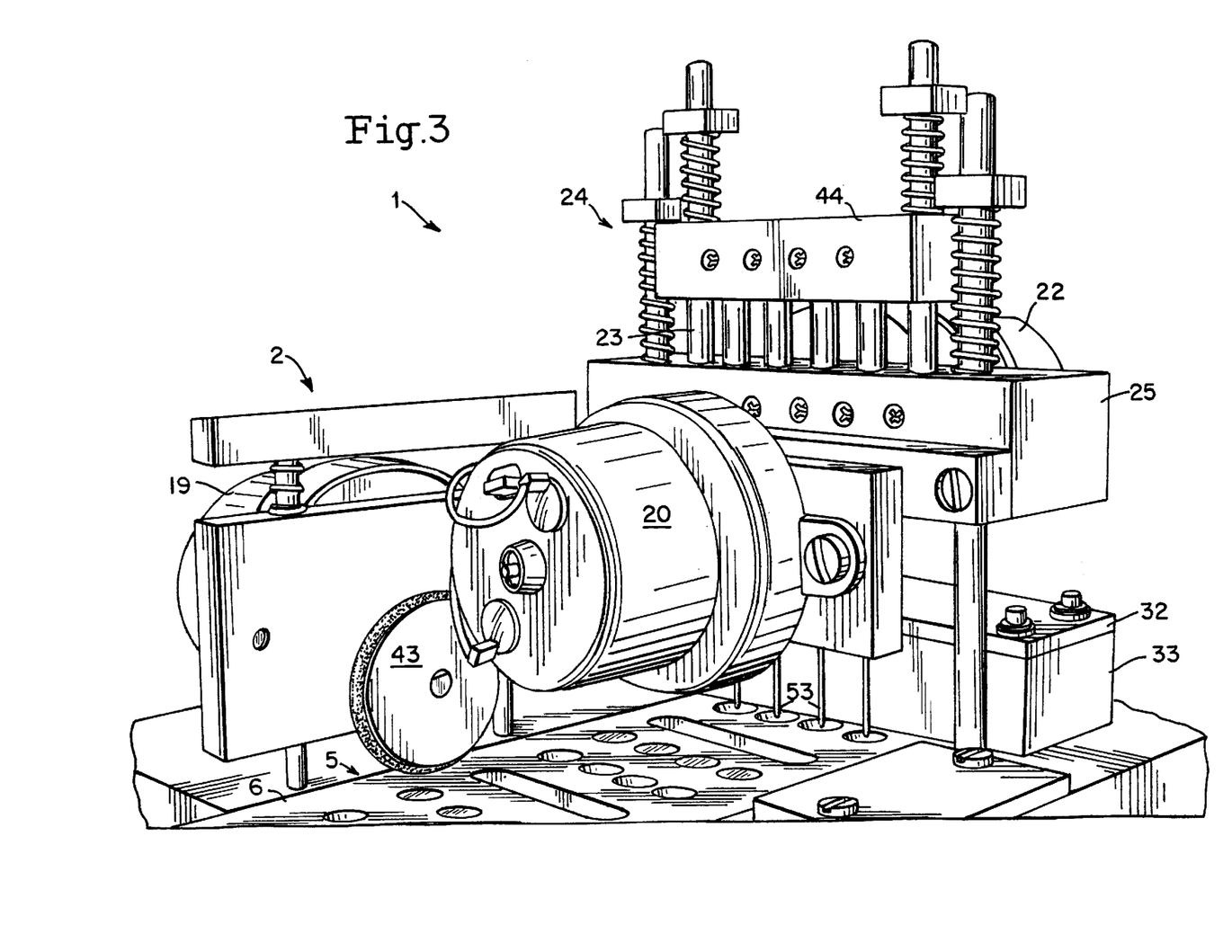
FIG. 3 is a close up angular view of the drive unit.
Figure 4:
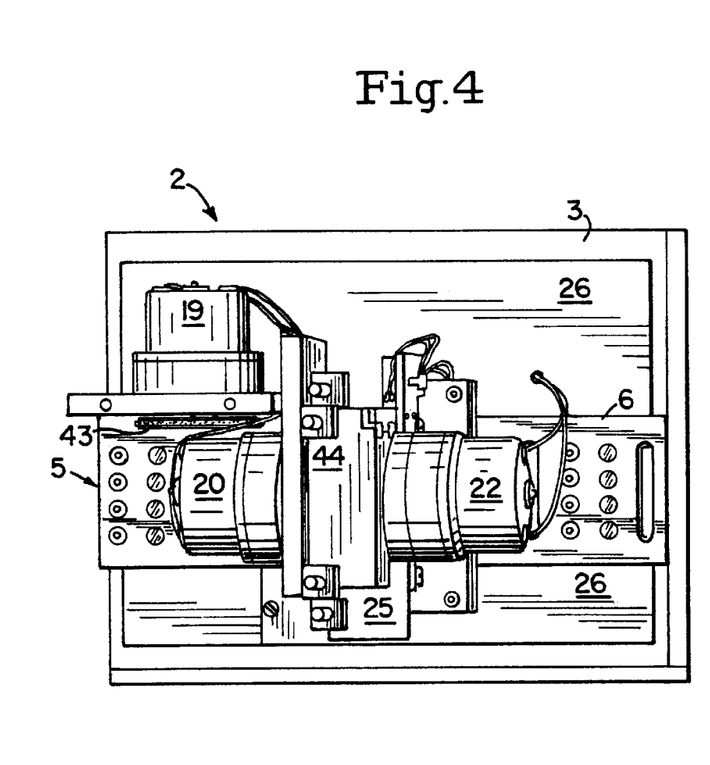
FIG. 4 is an overhead view of the invention.
Figure 5:
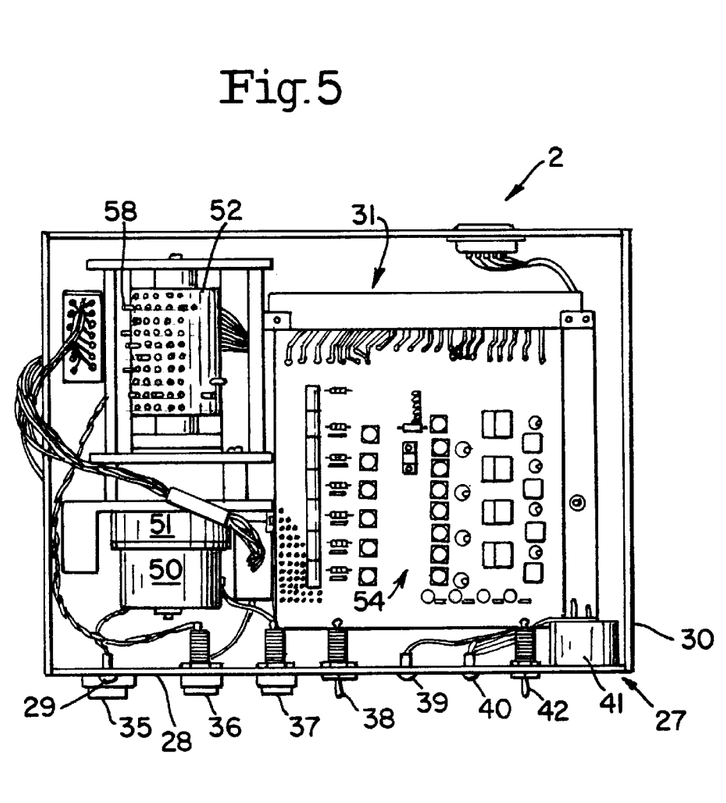
FIG. 5 is an overhead view of the interior of the invention.
Figure 6A:
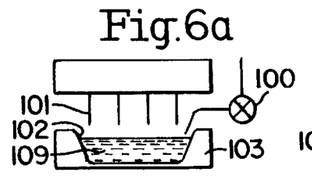
FIGS. 6a–6i is a schematic illustration of the sequencing and sampling process.
Figure 6B:
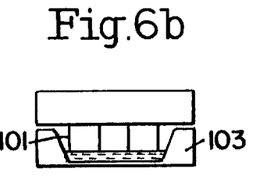
Figure 6C:
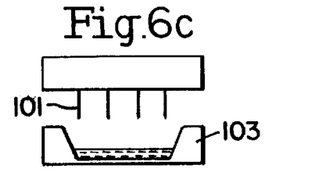
Figure 6D:
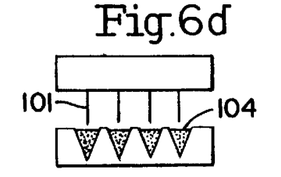
Figure 6E:
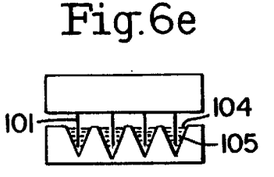
Figure 6F:
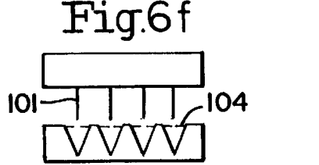
Figure 6G:
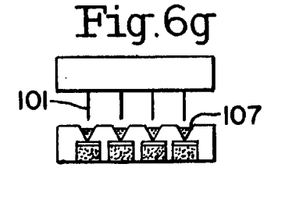
Figure 6H:
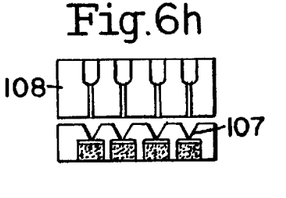
Figure 6I:
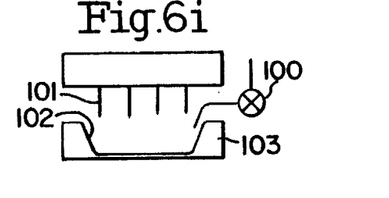

This sequence is best illustrated in FIGS. 6a–6i. In 6a, the solenoid valve 100 associated with the air sampler is actuated to dispense 400 µl of sample 109 into the reservoir well. The syringe tips 101 are lowered into the reservoir well 102 (FIG. 6a), and a 75 µl sample is drawn into each syringe. The syringe tips 101 are then raised (FIG. 6c) and the matrix 103 is advanced to the next position (FIG. 6d). The syringe tips are then again lowered (FIG. 6e), piercing the foil seals 104, and samples are expelled to reconstitute the lyophilized reaction mixture 105 which is then drawn back up into the syringes. The syringe tips are then raised again (6f), and the matrix is advanced to the next position where reaction fluid is delivered to the membrane wells 107 (FIG. 6g). The matrix is advanced to the next position (6h), situating the membrane wells under the four channel reader head 108 where reflectance levels are read and processed. The reading and processing of the reflectance levels should take about 5 seconds. In the final step (FIG. 6i), the next reservoir well is positioned below the syringe tips in preparation for a repetitive cycle.

Many modifications and variations of the present invention are possible in light of the above teachings. It is, therefore, to be understood within the scope of the appended claims the invention may be protected otherwise than as specifically described.

What is claimed is:

1. A biochemical detection system for rapid determination of the presence of toxins, bacteria, and other substances comprising:

- a sampling matrix, said sampling matrix comprising a rectangularly shaped tray having a plurality of rows, a first said row forming a single trough reservoir well, a second said row having a plurality of individual wells, said individual wells of said second row containing a lyophilized reaction mixture, said wells containing said lyophilized reaction mixture being covered by a secured covering, and a third row containing capture membrane wells comprising a flow through membrane which allows passage of unreacted conjugate through the membrane and captures an analyte-conjugate complex on a surface of said membrane;
- a drive unit, said drive unit comprising a plurality of syringes used to collect and expel samples and reagents, said syringes containing plungers,
- a motor for forwardly advancing the sampling matrix;
- a second motor for raising and lowering said syringes;
- a third motor for raising and lowering said plungers within said syringes to draw up and expel reagents and samples;
- a device for reading and detecting positive results;
- a device for timing and regulating sampling allowing for the continuous testing of said samples, without the need for human monitoring or operation of said system.

2. The biological detection system of claim 1, wherein said system is portable.

3. The biological detection system of claim 2, wherein said system can operate on a 9 volt battery.

4. The biological detection system of claim 1, wherein the device for timing and regulating sampling the operation of the functions of the biological detection system is a drum programmer and a motor which drives said drum programmer.

5. The biological detection system of claim 4, further comprising activation pins positioned on said drum programmer.

6. The biological detection system of claim 5, further comprising a plurality of micro switches, each said micro switch associated with a specific mechanical or switching operation, each said micro switch being activated by corresponding said pins on the drum programmer, to supply power to distribution points at appropriate time intervals.

7. The biological detection system of claim 2, wherein a device for reading and detecting said positive results of said samples comprises a reflectance detector unit which projects light onto a reaction membrane surface and reads reflected light with a photosensor.

8. The biochemical detection system of claim 1, wherein said membrane is coated with an antibody so that a sandwich assay results.

9. The biochemical detection system of claim 1, wherein said membrane is coated with an antigen so that a sandwich assay results.

10. The biochemical detection system of claim 1, wherein said membrane is coated with an antibody coated latex resulting in a sandwich assay.

11. The biochemical detection system of claim 1, wherein said membrane is coated with an antigen coated latex resulting in a sandwich assay.

12. The biochemical detection system of claim 1, wherein said membrane causes a trapping of an antigen-antibody labeled complex by charge.

13. The biochemical detection system of claim 1, wherein said membrane causes a trapping of an antigen-antibody labeled complex by size.

\* \* \* \* \*

UNITED STATES PATENT AND TRADEMARK OFFICE
CERTIFICATE OF CORRECTION

PATENT NO. : 6,146,591
DATED : November 14, 2000
INVENTOR(S) : David C. Miller

It is certified that error appears in the above-identified patent and that said Letters Patent is hereby corrected as shown below:

Column 3,
Line 18 change "was" to -- is --;
Line 41 change "The" to -- the --;
Line 60 change "25" to -- 21 --;

Column 4,
Line 4, change "reflectanc" to -- reflectance --;
Line 5, change "17" to -- 16 --.
Line 33, change "was" to -- is --;
Line 35, change "were" to -- are --;
Line 64, change "drug" to -- drum --;

Column 5,
Line 6, change "was" to -- is --;
Line 8, change "was" to -- is --; and
Line 11, change "turned" to -- turns --.

Signed and Sealed this

Twenty-fourth Day of July, 2001

*Attest:*

*Attesting Officer*

NICHOLAS P. GODICI
*Acting Director of the United States Patent and Trademark Office*